(12) United States Patent
Kane et al.

(10) Patent No.: US 10,980,454 B2
(45) Date of Patent: Apr. 20, 2021

(54) SYSTEMS AND METHODS FOR DETERMINING PRESENCE OF AN ANALYTE USING AN IMPLANTABLE MEDICAL DEVICE

(71) Applicant: Cardiac Pacemakers, Inc., St. Paul, MN (US)

(72) Inventors: Michael J. Kane, St. Paul, MN (US); Keith R. Maile, New Brighton, MN (US); Jeffrey E. Stahmann, Ramsey, MN (US)

(73) Assignee: Cardiac Pacemakers, Inc., St Paul, MN (US)

( * ) Notice: Subject to any disclaimer, the term of this patent is extended or adjusted under 35 U.S.C. 154(b) by 476 days.

(21) Appl. No.: 15/672,955

(22) Filed: Aug. 9, 2017

(65) Prior Publication Data
US 2018/0055426 A1 Mar. 1, 2018

Related U.S. Application Data

(60) Provisional application No. 62/380,228, filed on Aug. 26, 2016.

(51) Int. Cl.
*A61B 5/1455* (2006.01)
*A61B 5/145* (2006.01)
(Continued)

(52) U.S. Cl.
CPC ........ *A61B 5/14546* (2013.01); *A61B 5/1459* (2013.01); *A61B 5/14532* (2013.01);
(Continued)

(58) Field of Classification Search
None
See application file for complete search history.

(56) References Cited

U.S. PATENT DOCUMENTS 6,330,464 B1    12/2001    Colvin et al.
6,427,082 B1 *    7/2002    Nordstrom ........... A61B 5/0071
                                                                         250/461.2

(Continued)

FOREIGN PATENT DOCUMENTS

JP    2009-537247    10/2009
JP    2010-539484    12/2010
(Continued)

OTHER PUBLICATIONS

International Search Report and Written Opinion issued in PCT/US2017/046116, dated Oct. 30, 2017, 13 pages.

*Primary Examiner* — Marjan Fardanesh
(74) *Attorney, Agent, or Firm* — Faegre Drinker Biddle & Reath LLP (57) ABSTRACT

Systems and methods to determine presence of an analyte using an implantable medical device are disclosed. In an embodiment, a medical system includes an implantable medical device, a light source, an optical sensor and a processor. The implantable medical device includes an indicator tag, which is responsive to an analyte. The light source is configured to emit light onto the indicator tag, where the emitted light comprises at least one wavelength of light, and where the indicator tag emanates light, in response to the emitted light, that corresponds to whether the indicator tag is exposed the analyte. The optical sensor is configured to receive at least a portion of the emanated light, which includes at least one wavelength of light. And, the processor is configured to determine whether the indicator tag is exposed to the analyte based on the received light.

20 Claims, 5 Drawing Sheets

(51) Int. Cl.
  *A61B 5/1459* (2006.01)
  *A61B 5/1486* (2006.01)
  *A61B 5/00* (2006.01)

(52) U.S. Cl.
  CPC ...... *A61B 5/14556* (2013.01); *A61B 5/14865* (2013.01); *A61B 5/0031* (2013.01); *A61B 5/0097* (2013.01)

(56) References Cited

U.S. PATENT DOCUMENTS

| | | |
|---|---|---|
| 6,952,603 B2 | 10/2005 | Gerber et al. |
| 7,809,441 B2 | 10/2010 | Kane et al. |
| 9,364,662 B2 | 6/2016 | Foster et al. |
| 2002/0161286 A1 | 10/2002 | Gerber et al. |
| 2002/0197724 A1 | 12/2002 | Noronha et al. |
| 2007/0270674 A1 | 11/2007 | Kane et al. |
| 2007/0270675 A1 | 11/2007 | Kane et al. |
| 2009/0076353 A1 | 3/2009 | Carpenter et al. |
| 2013/0131765 A1 | 5/2013 | Polkinghorne et al. |
| 2013/0211213 A1 | 8/2013 | Dehennis et al. |
| 2014/0018644 A1 | 1/2014 | Colvin, Jr. et al. |
| 2014/0266776 A1 | 9/2014 | Miller et al. |
| 2014/0316482 A1 | 10/2014 | Kane et al. |
| 2016/0038743 A1 | 2/2016 | Foster et al. |

FOREIGN PATENT DOCUMENTS

| | | |
|---|---|---|
| JP | 2015-522300 A | 8/2015 |
| WO | 2007110867 A2 | 10/2007 |
| WO | 2013119951 A2 | 8/2013 |
| WO | 2016025297 A2 | 2/2016 |
| WO | 2016059635 A1 | 4/2016 |

\* cited by examiner

SYSTEMS AND METHODS FOR DETERMINING PRESENCE OF AN ANALYTE USING AN IMPLANTABLE MEDICAL DEVICE

CROSS-REFERENCE TO RELATED APPLICATION

This application claims priority to Provisional Application No. 62/380,228, filed Aug. 26, 2016, which is herein incorporated by reference in its entirety.

TECHNICAL FIELD

Embodiments of the present disclosure relate to medical devices and systems for determining presence of an analyte. More specifically, embodiments of the disclosure relate to systems and methods for determining the presence of an analyte using one or more indicator tags of an implantable medical device (IMD).

BACKGROUND

The onset or occurrence of a medical condition may be determined by determining the presence of an analyte and/or measuring one or more analyte concentrations. However, many conventional systems and methods that measure analytes to determine one or more medical conditions are oftentimes transient in time. For example, to determine the onset of a hyperglycemic event or a hypoglycemic event, subjects may be required to prick their fingers to determine their glucose levels. Many subjects, however, may either forget to check their glucose levels or not check their glucose levels often enough to prevent a hyperglycemic or a hypoglycemic event. As such, subjects may experience adverse events due to blood sugar that is either too high or too low. Accordingly, there is a need in the art for alternative systems and methods for determining the presence of an analyte and/or an analyte concentration of a subject.

SUMMARY

Embodiments of the disclosure relate to systems and methods for determining the presence of an analyte using one or more indicator tags disposed on an implantable medical device (IMD). Example embodiments include the following.

In an Example 1, a medical system comprises: an implantable medical device comprising an indicator tag, wherein the indicator tag is responsive to an analyte; a light source configured to emit light onto the indicator tag, wherein the emitted light comprises at least one wavelength of light and wherein the indicator tag emanates light, in response to the emitted light, that corresponds to whether the indicator tag is exposed the analyte; an optical sensor configured to receive light, the received light comprising at least a portion of the emanated light, wherein the received light comprises at least one wavelength of light; and a processor communicatively coupled to the optical sensor, wherein the processer is configured to determine whether the indicator tag is exposed to the analyte based on the received light.

In an Example 2, the medical system of Example 1, wherein the light source and the optical sensor are incorporated into the implantable medical device.

In an Example 3, the medical system of Example 1, wherein the light source is incorporated into a different device than the implantable medical device; wherein the optical sensor is incorporated into the implantable medical device; wherein the emitted light comprises at least two pulses of light; wherein the received light comprises a first received light pulse, the first received light pulse comprising a light pulse emanated by the indicator tag in response to a first emitted light pulse of the at least two pulses of light; and wherein the processor is configured to transition to a higher-power state in response to the optical sensor receiving the first received light pulse.

In an Example 4, the medical system of any of Examples 1-3, wherein the implantable medical device comprises a waveguide configured to transmit the received light to the optical sensor.

In an Example 5, the medical system of Example 1, wherein the light source is incorporated into the implantable medical device and the optical sensor is incorporated into a different device than the implantable medical device.

In an Example 6, the medical system of any of Examples 1-2 and 5, wherein the implantable medical device comprises a waveguide configured to transmit the emitted light to the indicator tag.

In an Example 7, the medical system of Example 1, wherein the light source is incorporated into a different device than the implantable medical device; wherein the optical sensor is incorporated into a different device than the implantable medical device; wherein the emitted light comprises at least two pulses of light; wherein the received light comprises a first received light pulse, the first received light pulse comprising a light pulse emanated by the indicator tag in response to a first emitted light pulse of the at least two pulses of light; and wherein the processor is configured to transition to a higher-power state in response to the optical sensor receiving the first received light pulse.

In an Example 8, the medical system of any of Examples 1-7, wherein the optical sensor comprises a plurality of photodetectors, wherein each of the plurality of photodetectors are coupled to a respective filter of a plurality of filters, wherein a filter of the plurality of filters is configured to allow only one wavelength of light to pass through the filter.

In an Example 9, the medical system of any of Examples 1-8, wherein the processor is configured to determine whether the indicator tag is exposed to the analyte based on the received light by determining a ratio of at least one of: an intensity of the received light to an intensity of the emitted light and a wavelength of the received light to a wavelength of the emitted light.

In an Example 10, the medical system of any of Examples 1-9, wherein the emitted light and the received light comprise at least two wavelengths of light; and wherein the processor is configured to determine whether the indicator tag is exposed to the analyte based on the received light by: determining a first absorption of a first wavelength of the at least two wavelengths of light by the indicator tag, determining a second absorption of a second wavelength of the at least two wavelengths of light by the indicator tag and comparing the first absorption to the second absorption.

In an Example 11, the medical system of any of Examples 1-10, wherein the indicator tag is responsive to the analyte by changing the indicator tag's fluorescence when exposed to the analyte; and wherein the processor is configured to determine whether the indicator tag is exposed to the analyte based on the received light by determining the indicator tag's fluorescence based on the received light.

In an Example 12, the medical system of any of Examples 1-11, wherein the processor is configured to determine whether the indicator tag is exposed to the analyte based on the received light by determining a fluorescence lifetime effect of the received light.

In an Example 13, a method comprises: exposing an indicator tag to light, wherein the light comprises at least one wavelength of light, wherein the indicator tag emanates light, in response to being exposed to the light, and wherein the emanated light corresponds to whether the indicator tag is exposed the analyte; receiving at least a portion of the emanated light using an optical sensor, wherein the received light comprises at least one wavelength of light; and determining, using a processor, whether the indicator tag is exposed to the analyte based on the received light.

In an Example 14, the method of Example 13, wherein the exposed light and the received light comprise at least two wavelengths of light and wherein whether the indicator tag is exposed to the analyte based on the received light comprises: determining a first absorption of a first wavelength of the at least two wavelengths by the indicator tag, determining a second absorption of a second wavelength of the at least two wavelengths by the indicator tag and comparing the first absorption to the second absorption.

In an Example 15, the method of any of Examples 13 and 14, wherein the indicator tag is responsive to the presence of the analyte by changing the indicator tag's fluorescence when exposed to different concentrations of the analyte and wherein determining whether the indicator tag is exposed to the analyte based on the received light comprises at least one of: determining the indicator tag's fluorescence based on the received light and determining a fluorescence lifetime effect of the received light.

In an Example 16, a medical system comprises: an implantable medical device comprising an indicator tag, wherein the indicator tag is responsive to an analyte; a light source configured to emit light onto the indicator tag, wherein the emitted light comprises at least one wavelength of light and wherein the indicator tag emanates light, in response to the emitted light, that corresponds to whether the indicator tag is exposed the analyte; an optical sensor configured to receive light, the received light comprising at least a portion of the emanated light, wherein the received light comprises at least one wavelength of light; and a processor communicatively coupled to the optical sensor, wherein the processer is configured to determine whether the indicator tag is exposed to the analyte based on the received light.

In an Example 17, the medical system of Example 16, wherein the light source and the optical sensor are incorporated into the implantable medical device.

In an Example 18, the medical system of Example 16, wherein the light source is incorporated into a different device than the implantable medical device; and wherein the optical sensor is incorporated into the implantable medical device.

In an Example 19, the medical system of Example 18, wherein the implantable medical device comprises a waveguide configured to transmit the received light to the optical sensor.

In an Example 20, the medical system of Example 16, wherein the light source is incorporated into the implantable medical device and the optical sensor is incorporated into a different device than the implantable medical device.

In an Example 21, the medical system of Example 20, wherein the implantable medical device comprises a waveguide configured to transmit the emitted light to the indicator tag.

In an Example 22, the medical system of Example 16, wherein the light source and the optical sensor are incorporated into a different device than the implantable medical device.

In an Example 23, the medical system of Example 16, wherein the optical sensor comprises a plurality of photodetectors, wherein each of the plurality of photodetectors are coupled to a respective filter of a plurality of filters, wherein a filter of the plurality of filters is configured to allow only one wavelength of light to pass through the filter.

In an Example 24, the medical system of Example 16, wherein the processor is configured to determine whether the indicator tag is exposed to the analyte based on the received light by determining a ratio of at least one of: an intensity of the received light to an intensity of the emitted light and a wavelength of the received light to a wavelength of the emitted light.

In an Example 25, the medical system of Example 16, wherein the emitted light and the received light comprise at least two wavelengths of light; and wherein the processor is configured to determine whether the indicator tag is exposed to the analyte based on the received light by: determining a first absorption of a first wavelength of the at least two wavelengths of light by the indicator tag, determining a second absorption of the at least two wavelengths of light by the indicator tag and comparing the first absorption to the second absorption.

In an Example 26, the medical system of Example 16, wherein the indicator tag is responsive to the presence of the analyte by changing the indicator tag's fluorescence when exposed the analyte; and wherein the processor is configured to determine whether the indicator tag is exposed to the analyte based on the received light by determining the indicator tag's fluorescence based on the received light.

In an Example 27, the medical system of Example 16, wherein the processor is configured to determine whether the indicator tag is exposed to the analyte based on the received light by determining a fluorescence lifetime effect of the received light.

In an Example 28, the medical system of Example 16, wherein the emitted light comprises at least two pulses of light; wherein the received light comprises a first received light pulse, the first received light pulse comprising a light pulse emanated by the indicator tag in response to a first emitted light pulse of the at least two pulses of light; and wherein the processor is configured to transition to a higher-power state in response to the optical sensor receiving the first received light pulse.

In an Example 29, a method comprises: exposing an indicator tag to light, wherein the light comprises at least one wavelength of light, wherein the indicator tag emanates light, in response to being exposed to the light, and wherein the emanated light corresponds to whether the indicator tag is exposed the analyte receiving at least a portion of the emanated light using an optical sensor, wherein the received light comprises at least one wavelength of light; and determining, using a processor, whether the indicator tag is exposed to the analyte based on the received light.

In an Example 30, the method of Example 29, wherein the exposed light and the received light comprise at least two wavelengths of light and wherein whether the indicator tag is exposed to the analyte based on the received light comprises: determining a first absorption of a first wavelength of the at least two wavelengths by the indicator tag, determining a second absorption of a second wavelength of the at least two wavelengths by the indicator tag and comparing the first absorption to the second absorption.

In an Example 31, the method of Example 29, wherein the indicator tag is responsive to the presence of the analyte by changing the indicator tag's fluorescence when exposed to different concentrations of the analyte and wherein determining whether the indicator tag is exposed to the analyte based on the received light comprises at least one of: determining the indicator tag's fluorescence based on the received light and determining a fluorescence lifetime effect of the received light.

In an Example 32, the method of Example 29, wherein determining the presence of the analyte based on the received light comprises determining a fluorescence lifetime effect of the received light.

In an Example 33, the method of Example 29, wherein at least one of: the optical sensor and the indicator tag are coupled together using a waveguide, and the light source and the indicator tag are coupled together using a waveguide.

In an Example 34, the method of Example 29, further comprising: filtering the emanated light using at least one filter before the emanated light is received by the optical sensor.

In an Example 35, the method of Example 29, wherein the light comprises at least two pulses of light; wherein the received light comprises a first received light pulse, the first received light pulse comprising a light pulse emanated by the indicator tag in response to a first emitted light pulse of the at least two pulses of light; and sending a signal to the processor in response to the optical sensor receiving the first received light pulse, wherein the processor transitions from a lower-power state to a higher-power state in response to receiving the signal.

While multiple embodiments are disclosed, still other embodiments of the present disclosure will become apparent to those skilled in the art from the following detailed description, which shows and describes illustrative embodiments of the disclosed subject matter. Accordingly, the drawings and detailed description are to be regarded as illustrative in nature and not restrictive.

While the disclosed subject matter is amenable to various modifications and alternative forms, specific embodiments have been shown by way of example in the drawings and are described in detail below. The intention, however, is not to limit the disclosed subject matter to the particular embodiments described. On the contrary, the disclosed subject matter is intended to cover all modifications, equivalents, and alternatives falling within the scope of the disclosed subject matter as defined by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

Figure 1:
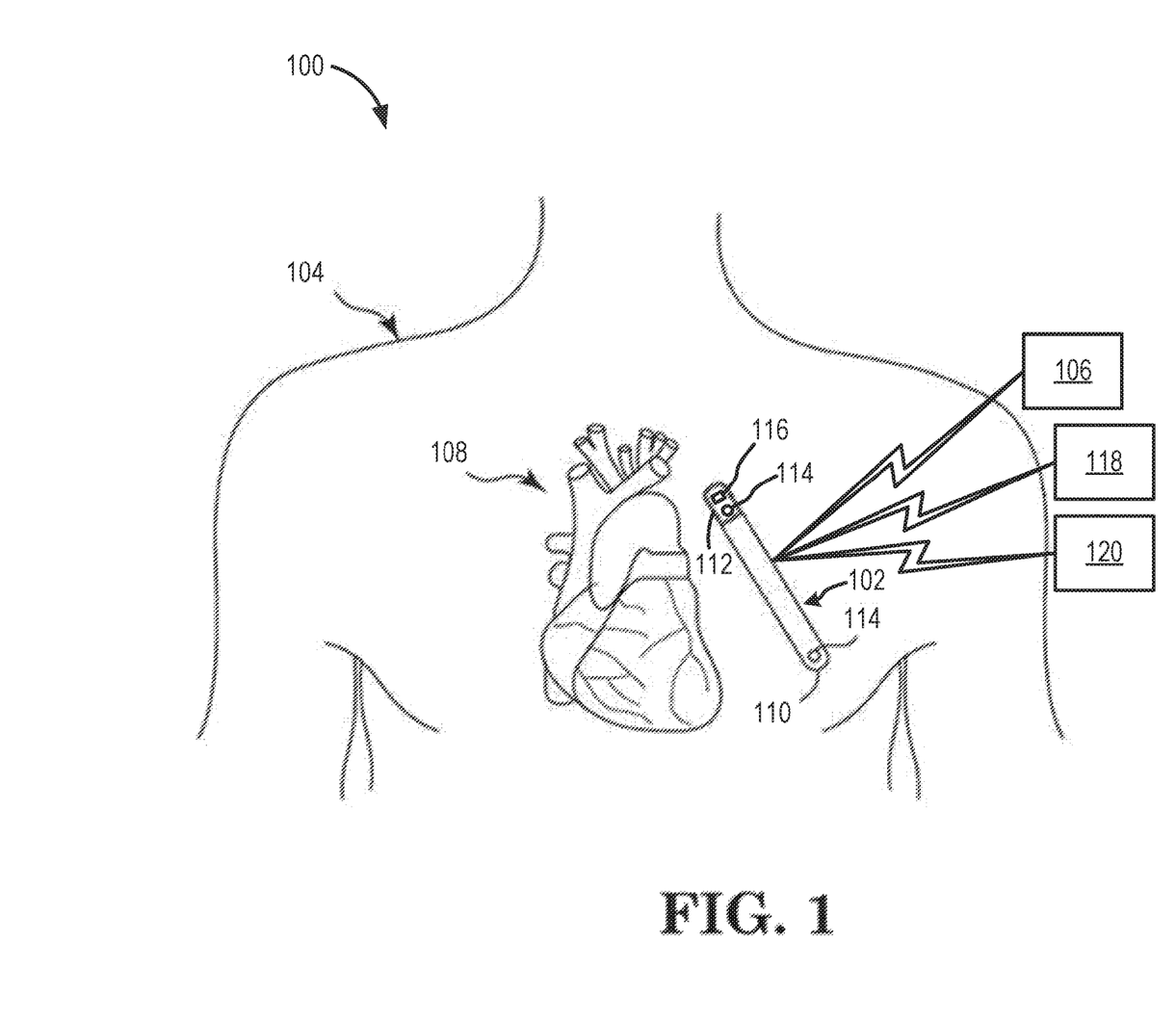
FIG. 1 is a schematic illustration of a system including an IMD for determining the presence of an analyte and/or an analyte concentration, in accordance with embodiments of the present disclosure.

FIG. 1 is a schematic illustration of a system 100 including an implantable medical device (IMD) 102 implanted within a subject's body 104 and configured to be communicatively coupled to a processor 106. The system 100 may be used to monitor (e.g., determine, sense and/or record) the presence or absence of an analyte and/or an analyte concentration in vivo of a subject in order to diagnose, and/or provide therapy to the subject in accordance with embodiments of the disclosure. In embodiments, the IMD 102 may be implanted subcutaneously within an implantation location or pocket, for example, in the subject's chest, abdomen, head, leg and/or arm, where the IMD 102 may be configured to monitor the presence or absence of an analyte and/or analyte concentrations. That is, for example, the IMD 102 may determine the presence or absence of an analyte and/or an analyte concentration in a subject's interstitial fluid, serous fluid, gastric fluid, blood, urine, an organ and/or the like. The one or more analytes and/or one or more analyte concentrations may be indicative of one or medical conditions associated with the subject's circulatory system, muscular system, skeletal system, nervous system, lymphatic system, respiratory system and/or endocrine system.

Additionally or alternatively, in embodiments, the IMD 102 may also be configured to monitor other physiological parameters associated with the subject's circulatory system 108. For example, the IMD 102 may be an implantable cardiac monitor (ICM) (e.g., an implantable diagnostic monitor (IDM), an implantable loop recorder (ILR), etc.) configured to monitor physiological parameters such as, for example, the subject's cardiac activation signals, heart sounds, pulsations of arteries, oxygen saturations, and/or the like. However, these are only examples and not meant to be limiting.

Additionally or alternatively, in embodiments, the IMD 102 may also be configured to monitor other physiological parameters associated with the subject's respiratory system. For example, the IMD 102 may be an implantable respiratory monitor (IRM) configured to monitor physiological parameters such as, for example, the subject's respiratory rate, tidal volume, respiratory pattern, airflow, oxygen saturations, and/or the like. However, these are only examples and not meant to be limiting.

Additionally or alternatively, in embodiments, the IMD 102 may be configured to monitor physiological parameters that may include one or more signals indicative of a subject's physical activity level and/or metabolic level, such as an acceleration signal. In embodiments, the IMD 102 may be configured to monitor physiological parameters associated with one or more other organs, systems, and/or the like. For example, the IMD 102 may include sensors or circuitry for detecting cardiac system signals, circulatory system signals, nervous system signals, respiratory system signals, and/or signals related to subject activity.

Additionally or alternatively, in embodiments, the IMD 102 may be configured to sense intrathoracic impedance, from which various respiratory parameters may be derived, including, for example, respiratory tidal volume and minute ventilation. In embodiments, the IMD 102 may be configured to sense cardiac impedance, from which various cardiac parameters may be derived, including, for example, left and right ventricular activity. Sensors and associated circuitry may be incorporated in connection with the IMD 102 for detecting one or more body movement, body posture and/or position related signals. For example, accelerometers and/or GPS devices may be employed to detect tremors, shaking, imbalance patterns, subject activity, subject location, body orientation, and/or torso position. In embodiments, one or more body movements, body postures and/or position related signals may be used as a secondary and/or confirmatory signal to other signals, for example, the signal indicative of an analyte and/or analyte concentration.

For purposes of illustration, and not of limitation, various embodiments of devices that may be used to monitor physiological parameters in accordance with the present disclosure are described herein in the context of IMDs that may be implanted under the skin in the chest region of a subject. In embodiments, however, the IMD 102 may include any type of IMD, any number of different components of an implantable system, and/or the like having a housing and being configured to be implanted in a subject's body 104. For example, the IMD 102 may include a control device, a monitoring device, a pacemaker, an implantable cardioverter defibrillator (ICD), a subcutaneous implantable cardioverter defibrillator (S-ICD), a leadless implantable cardioverter defibrillator (L-ICD), a cardiac resynchronization therapy (CRT) device, a neural stimulation device, and/or the like, and may be an implantable medical device known in the art or later developed, for providing therapy and/or diagnostic data about the subject's body and/or the IMD 102. In various embodiments, the IMD 102 may include both defibrillation and pacing/CRT capabilities (e.g., a CRT-D device).

The IMD 102 may be configured to monitor at regular intervals, continuously, and/or in response to a detected event. In embodiments, such a detected event may be detected by one or more sensors of the IMD 102, another IMD (not shown), an external device (not shown), and/or the like. In addition, the IMD 102 may be configured to detect a variety of analytes and/or concentrations thereof that may be used in connection with various diagnostic, therapeutic, and/or monitoring implementations.

As shown, the IMD 102 may include a housing 110 having a header 112 that is arranged near an end of the IMD 102. The housing 110 may include any number of different shapes, sizes, and/or features. In embodiments, the IMD 102 may include any number of electrodes 114 and/or other types of sensors such as, e.g., sound sensors, pressure sensors, impedance sensors, optical sensors, thermometers, barometers, motion or impact sensors (e.g., accelerometers, inertial measuring units (IMUs)), and/or the like) in any number of various types of configurations.

In embodiments, the IMD 102 may include one or more indicator tags 116 that are responsive to whether the indicator tag 116 is exposed to an analyte (i.e., the presence or absence of an analyte) and/or an analyte concentration in vivo of the subject. In embodiments, the indicator tag 116 is in communication with the portion of the subject in which the analyte may be present. For example, the indicator tag 116 may be in communication with the subject's interstitial fluid, serous fluid, gastric fluid, blood, urine, an organ, and/or the like that may include the analyte. To do so, the indicator tag 116 may be located on a portion of the IMD 102 such that the indicator tag 116 is in communication the subject's interstitial fluid, serous fluid, gastric fluid, blood, urine, an organ, breath and/or the like that may include the analyte. For example, in embodiments, the indicator tag 116 may be located on a portion of the IMD 102 that is directly exposed to the subject's interstitial fluid, serous fluid, gastric fluid, blood, urine, an organ, and/or the like that may include the analyte. As another example, the indicator tag 116 may be located on a portion of the IMD 102 and covered by a layer of material that is permeable to the analyte. In embodiments, the indicator tag 116 may be covered by a layer of material to prolong the useful life of the indicator tag 116.

In embodiments, the indicator tag 116 may include one or more indicator tags 116. In embodiments where more than one indicator tag 116 is included, one indicator tag 116 may be used as a redundancy check for the other indicator tag 116. Additionally or alternatively, each indicator tag 116 may be responsive to the same analyte and/or analyte concentration; or, each indicator tag 116 may be responsive to different analytes and/or different analyte concentrations. Additionally or alternatively, in embodiments, one indicator tag 116 may be covered by a surface that decays over time so that a first indicator tag 116 will be used for a first period of time and a second indicator tag 116 that is covered by a surface that decays over time will be used for a second period of time, after the first period of time. While two indicator tags 116 are discussed, there may be three, four, five, six, etc. indicator tags 116. Including indicator tags 116 that are used during different time periods may prolong the useful life of the IMD 102.

To determine one or more properties of the indicator tag 116 that may be responsive to the presence or absence of an analyte and/or an analyte concentration, the indicator tag 116 may be exposed to light emitted from a light source 118. In response to being exposed to light, the indicator tag 116 may emanate light that is indicative of the one or more properties of the indicator tag 116. In embodiments, the light emanated from the indicator tag 116 may be re-radiated light via fluorescence. In embodiments, the light emanated from the indicator tag 116 may be light that is reflected by the indicator tag 116. Examples of properties of the indicator tag 116 that may change in response to the presence or absence of an analyte and/or analyte concentration include, but are not limited to, the type and/or amount of light that the indicator tag 116 absorbs and/or reflects, the fluorescence of the indicator tag 116 and/or the fluorescence lifetime effect. These examples are explained in more detail below in relation to FIG. 2.

The emanated light from the indicator tag 116 may be sensed using an optical sensor 120. The sensed light by the optical sensor 120 may be stored in memory and/or communicated to the processor 106 via one or more signals. The processor 106 is configured to determine whether the indicator tag 116 is exposed to an analyte (i.e., the presence or absence of an analyte) and/or an analyte concentration based on the received signal from the optical sensor 120.

Additionally or alternatively, the IMD 102 may be configured to transition from a lower-power state to a higher-power state in response to sensing a light pulse from the optical sensor 120. After converting to a higher-power state, the processor 106 may be configured to determine the presence or absence of an analyte and/or one or more analyte concentrations based on the received signals. Additionally or alternatively, the IMD 102 may be configured to transition from a lower-power state to a higher-power state after receiving a signal via a non-wireless and/or wireless communication link. In embodiments, the IMD 102 may transition from a higher-power state to a lower-power state after determining the presence or absence of an analyte and/or one or more analyte concentrations.

In embodiments, the processor 106, the light source 118 and/or the optical sensor 120 may be incorporated into the IMD 102 or external to the IMD 102. For example, in embodiments where the processor 106, the light source 118 and/or the optical sensor 120 are external to the IMD 102, the processor 106, the light source 118 and/or the optical sensor 120 may be incorporated into another IMD (not shown). Alternatively, in embodiments where the processor 106, the light source 118 and/or the optical sensor 120 are external to the IMD 102, the processor 106, the light source 118 and/or the optical sensor 120 may be positioned on the subject, near the subject, or in any location external to the subject.

In embodiments, the light source 118, optical sensor 120 and indicator tag 116 may operate within the visible light spectrum. In other embodiments, the light source 118, optical sensor 120 and indicator tag 116 may operate within the infrared spectrum. In yet other embodiments, the light source 118, optical sensor 120 and indicator tag 116 may operate within the ultraviolet spectrum. In still other embodiments, the light source 118, optical sensor 120 and indicator tag 116 may operate within a combination of the visible, infrared and/or ultraviolet light spectrum. Accordingly, in embodiments, the scope of the term light in this application includes the infrared, visible and ultraviolet portions of the electromagnetic spectrum.

In embodiments, the IMD 102 and the processor 106 may communicate through a non-wireless and/or wireless communication link. For example, the IMD 102 and the processor 106 may be communicatively coupled through a short-range radio link, such as Bluetooth, IEEE 802.11, and/or a proprietary wireless protocol. The term "communication link" may refer to an ability to communicate some type of information in at least one direction between at least two devices, and should not be understood to be limited to a direct, persistent, or otherwise limited communication channel. That is, according to embodiments, the communication link may be a persistent communication link, an intermittent communication link, an ad-hoc communication link, and/or the like. The communications link may facilitate uni-directional and/or bi-directional communication between the IMD 102 and the processor 106. Data and/or control signals may be transmitted between the IMD 102 and the processor 106 to coordinate the functions of the IMD 102 and/or the processor 106. In embodiments, subject data may be downloaded from one or more of the IMD 102 and the processor 106 periodically or on command. The physician and/or the subject may communicate with the IMD 102 and the processor 106, for example, to acquire analyte data and/or to initiate, terminate, or modify the determination of: the presence or absence of an analyte, an analyte concentration and/or to administer therapy.

The illustrative system 100 shown in FIG. 1 is not intended to suggest any limitation as to the scope of use or functionality of embodiments of the subject matter disclosed throughout this disclosure. Neither should the illustrative system 100 be interpreted as having any dependency or requirement related to any single component or combination of components illustrated in FIG. 1. For example, in embodiments, the illustrative system 100 may include additional components. Additionally, any one or more of the components depicted in FIG. 1 can be, in embodiments, integrated with various ones of the other components depicted therein (and/or components not illustrated). Any number of other components or combinations of components can be integrated with the illustrative system 100 depicted in FIG. 1, all of which are considered to be within the ambit of this disclosure.

Figure 2:
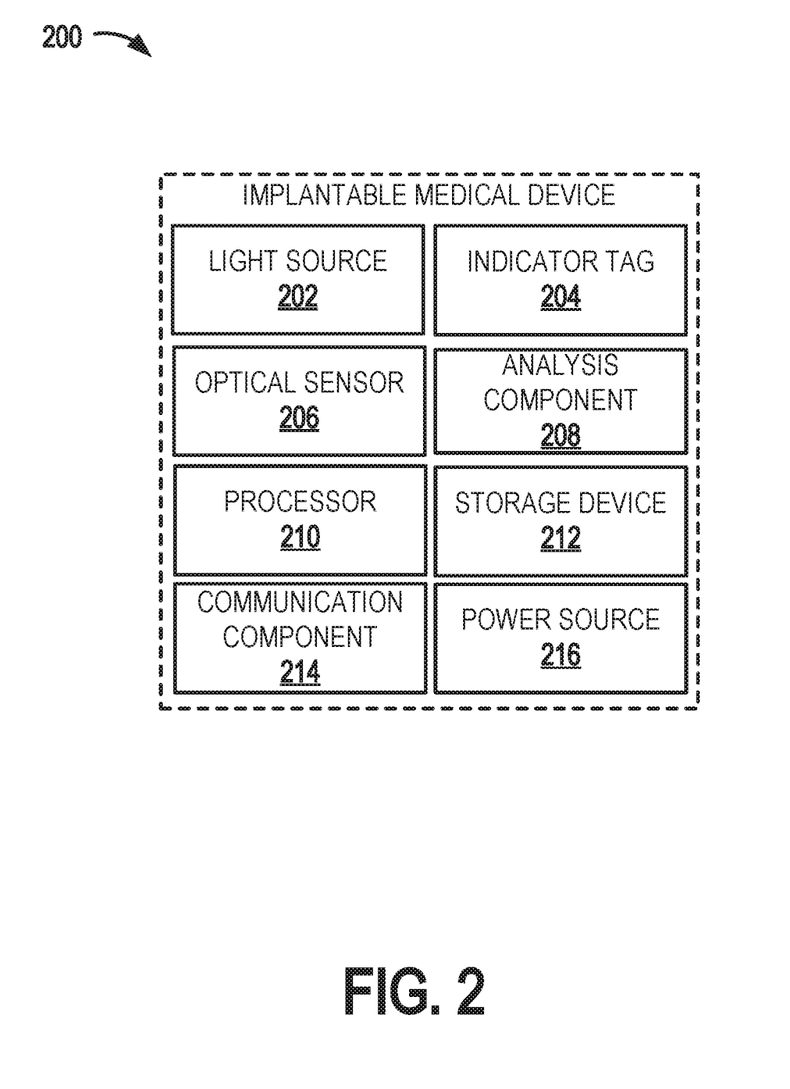
FIG. 2 is a block diagram depicting an illustrative medical system for determining the presence of an analyte and/or an analyte concentration, in accordance with embodiments of the present disclosure.

FIG. 2 is a block diagram depicting an illustrative implantable medical device 200 for determining the presence or absence of an analyte and/or an analyte concentration in vivo, in accordance with embodiments of the present disclosure. Embodiments may include more than one IMD 200. The IMD 200 may be, be similar to, include, or be included in, the IMD 102 depicted in FIG. 1. For example, the IMD 200 may be implanted in a subject's chest, abdomen head, leg and/or arm and/or may be implanted in interstitial fluid, serous fluid, gastric fluid, blood, urine, an organ and/or the like.

According to embodiments illustrated in FIG. 2, the IMD 200 includes a light source 202, an indicator tag 204, an optical sensor 206, an analysis component 208, a processor 210, a storage device 212, a communication component 214 and/or a power source 216.

In embodiments, the light source 202 may be, be similar to, include, or be included in, the light source 118 depicted in FIG. 1. The light source 202 is configured to emit light. In embodiments, the light emitted from the light source 202 may be continuous light, a light pulse and/or a series of more than one light pulse (e.g., two light pulses, three light pulses, etc.). In embodiments where a series of light pulses are emitted from the light source 202, the light pulses may be of different durations and/or intensities. In embodiments, a first light pulse of a series of light pulses may be used to transition the IMD 200 from a lower-power state to a higher-power state, as described below.

Additionally or alternatively, the light emitted from the light source 202 may be comprised of a single narrowband of wavelengths or more than one narrowband of wavelengths. In embodiments, the light emitted from the light source 202 may be two narrowband sources, three narrowband source, etc. Additionally or alternatively, in embodiments, more than one narrowband of wavelengths may be produced using an LED and a specific phosphor for the type of narrowband wavelength that is to be obtained. For example, the light emitted from the light source 202 may be white light comprised of more than one narrowband of wavelengths. The white light may be produced using a blue or ultraviolet light-emitting diode (LED) and a phosphor coating. The blue or ultraviolet photons generated by the blue or ultraviolet LED either travel through the phosphor layer unaltered, or they are converted into yellow photons in the phosphor layer. Some of the yellow photons may combine with the blue or ultraviolet photons to generate white light. A light source 202 that emits more than one narrowband of wavelengths may be used to reduce the likelihood that changes sensed by the optical sensor 206 are determined to be the presence or absence of an analyte and/or changes in an analyte concentration when instead the changes are due to either output changes of the light source 202 and/or path loss changes, as explained below.

The light emitted from the light source 202 is directed at the indicator tag 204. The light emitted from the light source 202 and directed at the indicator tag 204 may include more than one narrowband of wavelengths. The indicator tag 204 is exposed to at least a portion of the emitted light that is directed at the indicator tag 204. In response to being exposed to some or all of the emitted light from the light source 202, the indicator tag 204 is configured to emanate light. In embodiments, the light emanated from the indicator tag 204 may include more than one narrowband of wavelengths. In embodiments, the type and/or amount of light that the indicator tag 204 emanates may be responsive to the environment of the indicator tag 204. That is, as described above, the indicator tag 204 may vary the type and/or amount of light that it emanates in response to an analyte and/or an analyte concentration. In embodiments, the light emanated from the indicator tag 204 may be re-radiated light via fluorescence. In embodiments, the light emanated from the indicator tag 204 may be light that is reflected by the indicator tag 204.

In embodiments, the amount of light that is emanated by the indicator tag 204 may be responsive to the different wavelengths of light to which the indicator tag 204 is exposed, analytes to which the indicator tag 204 is exposed and/or analyte concentrations to which the indicator tag 204 is exposed. For example, in response to being exposed to an analyte, the indicator tag 204 may absorb more green light than red light and, therefore, may emanate more red light than green light. That is, the intensity of the green light that is emanated is greater than the intensity of the red light that is emanated. However, if the indicator tag 204 is not exposed to the analyte, the indicator tag 204 may absorb more red light than green light and, therefore, may emanate more green light than red light.

As another example, the fluorescence of the indicator tag 204 may change in response to the presence or absence of an analyte and/or an analyte concentration. For example, if the indicator tag 204 is not exposed to an analyte, the indicator tag 204 may have a first fluorescence color. However, in response to being exposed to an analyte, the indicator tag 204 may have a second fluorescence color.

As even another example, the fluorescence lifetime effect of the indicator tag 204 may change in response to the presence or absence of an analyte and/or an analyte concentration. That is, the emanated light by the indicator tag 204 may be delayed by different times that correspond to the presence or absence of an analyte and/or a concentration of an analyte. For example, if the indicator tag 204 is not exposed to an analyte, the emanated light from the indicator tag 204 may be delayed by a first time. However, in response to being exposed to an analyte, the indicator tag 204 may be delayed by a second time that is different than the first time.

In embodiments, the indicator tag 204 may be comprised of one or more of the following. In an embodiment, the indicator tag 204 may be comprised of a non-carrier ion selective sensing element, such that a fluoroionophore is covalently bonded to a suitable substrate. A fluoroionophore is a compound including both a fluorescent moiety and an ion complexing moiety. As an example, (6,7-[2.2.2]-cryptando-3-[2"-(5"-carboethoxy)thiophenyl]coumarin, a potassium ion selective fluoroionophore, can be covalently attached to an azlactone functional hydrophilic porous polyethylene membrane to produce a fluorescence-based $K^+$ non-carrier ion sensor. As another example, hydroxypyrene trisulfonate, a hydrogen ion selective fluoroionophore, can be covalently attached to an amine functional cellulose to produce a fluorescence-based pH non-carrier ion sensor. The fluoroionophore can be covalently bonded to a substrate by any useful reactive technique, which may depend upon the chemical functionality of the particular fluoroionophore. The substrate can, in turn, be attached to a backing membrane or layer. An exemplary class of fluoroionophores is the coumarocryptands. Coumarocryptands can include lithium specific fluoroionophores, sodium specific fluoroionophores, and potassium specific fluoroionophores. For example, lithium specific fluoroionophores can include (6,7-[2.1.1]-cryptando-3-[2"-(5"-carboethoxy)furyl]coumarin. Sodium specific fluoroionophores can include (6,7-[2.2.1]-cryptando-3-[2"-(5"-carboethoxy)furyl]coumarin. Potassium specific fluoroionophores can include (6,7-[2.2.2]-cryptando-3-[2"-(5"-carboethoxy)furyl]coumarin and (6,7-[2.2.2]-cryptando-3-[2"-(5"-carboethoxy)thiophenyl]coumarin.

In an embodiment, the indicator tag 204 may be a non-carrier potassium ion sensor. For example, the indicator tag 204 may include a sensing layer that includes 6,7-[2.2.2]-cryptando-3-[2"-(5"-carboxy)furyl]coumarin (FCCC) covalently bonded to a crosslinked amine functional cellulose membrane (CUPROPHAN™; Enka AG, Ohderstrasse, Germany), the sensing layer being adhered to a polycarbonate backing membrane by FLEXOBOND 430™ urethane adhesive and the backing membrane having coated thereon CW14™ pressure-sensitive adhesive on a release liner. Another specific example of a non-carrier potassium ion sensor includes a sensing layer that includes 6,7-[2.2.2]-cryptando-3-[2"-(5"-carboxy)furyl]coumarin covalently bonded to a crosslinked azlactone functional hydrogel with a linker such as a diamine linker. The sensing layer can then be photocrosslinked within the cavity of a substrate, such as a microwell, or the gel capsule of a satellite sensor. The term satellite sensor can be used to describe implanted chemical sensors that are remote from the pulse generator.

In an embodiment, the indicator tag 204 may be a non-carrier sodium ion sensor. For example, the indicator tag 204 may include a sensing layer having 6,7-[2.2.1]-cryptando-3-[2"-(5"-carboxy)furyl]coumarin covalently bonded to a crosslinked amine functional cellulose membrane (CUPROPHAN™; Enka AG, Ohderstrasse, Germany), the sensing layer being adhered to a polycarbonate backing membrane by FLEXOBOND 430™ urethane adhesive and the backing membrane having coated thereon CW14™ pressure-sensitive adhesive on a release liner.

In an embodiment, the indicator tag 204 may be a non-carrier hydrogen ion sensor. For example, the indicator tag 204 may include a sensing layer that includes hydroxypyrene trisulfonate covalently bonded to a crosslinked amine functional cellulose membrane (CUPROPHAN™; Enka AG, Ohderstrasse, Germany), the sensing layer being adhered to a polycarbonate backing membrane by FLEXO-BOND 430™ urethane adhesive and the backing membrane having coated thereon CW14™ pressure-sensitive adhesive on a release liner.

Additionally or alternatively, the indicator tag 204 may be a non-enzymatic acid (e.g., boronic acid) in a hydrogel, a glucose-responsive fluorescence hydrogel, AcetonaPhthone phenyl ethyl Propionate Hydroxyl Tungstate (APPHT), etc. Other examples that the indicator tag 204 may be comprised of are discussed in U.S. Pat. No. 11/383,933, entitled "Implantable Medical Device with Chemical Sensor and Related Methods," filed on May 17, 2006, the disclosure of which is hereby expressly incorporated herein by reference.

Analytes that the indicator tag 204 may be responsive to include, for example, creatinine, inflammatory markers (e.g. cytokines, C reactive protein), natriuretic proteins (e.g. ABP, BNP), lipids, bicarbonate, cardiac troponin, creatine phosphokinase, hexane, ketones, glucose, hemoglobin A1c, electrolytes (e.g., potassium, sodium), blood urea nitrogen, a hydrogen concentration (i.e., pH level), chloride, NT-proBNP, uric acid, lithium, digoxin and/or the like.

The indicator tag 204 may be adhered and/or bonded to the IMD 200 using one or more adhesives and/or bonding techniques for IMDs 200. Alternatively, in embodiments, the indicator tag 204 may be configured to adhere to the IMD 200 without the use of an adhesive. In embodiments, the indicator tag 204 may be located on a portion of the IMD 200 that may be directly exposed to an analyte. In embodiments, the indicator tag 204 may be covered by a layer that is permeable to the analyte. In embodiments, the indicator tag 204 may be covered by a layer to prolong the useful life of the indicator tag 204.

While only one indicator tag 204 is depicted in FIG. 2, in embodiments, more than one indicator tag 204 may be disposed on the outer surface of the IMD 200. In embodiments where more than one indicator tag 204 is included, one indicator tag 204 may be used as a redundancy check for the other indicator tag 204. Additionally or alternatively, each indicator tag 204 may be responsive to the same analyte and/or analyte concentration; or, each indicator tag 204 may be responsive to different analytes and/or different analyte concentrations. Additionally or alternatively, in embodiments, one indicator tag 204 may be covered by a surface that decays over time so that a first indicator tag 204 will be used for a first period of time and a second indicator tag 204 that is covered by a surface that decays over time will be used for a second period of time, after the first period of time. While two indicator tags 204 are discussed, there may be three, four, five, six, etc. indicator tags 204. Including indicator tags 204 that are used during different time periods may prolong the useful life of the MD 200.

In embodiments, the indicator tag 204 may include one or more filters (e.g., a bandpass filter) and/or be coupled to one or more filters for filtering out one or more wavelengths of light.

Additionally or alternatively, in embodiments, one or more waveguides may couple emitted light from the light source 202 to the indicator tag 204. In embodiments where the light source 202 emits more than one narrowband of wavelengths, a single waveguide may couple the emitted light from the light source 202 to the indicator tag 204. Alternatively a respective waveguide for each narrowband of wavelengths of light may couple the emitted light from the light source 202 to the indicator tag 204. In embodiments, the one or more waveguides may include a filter for filtering out one or more wavelengths of light.

In embodiments, any number of mitigation systems and methods may be used to increase useful life of the indicator tag 204 and/or the IMD 200. For example, the indicator tag 204 may be coated with a thin-film membrane. Other examples of mitigation systems and methods that may be used to increase the useful life of the indicator tag 204 and/or the IMD 200 are discussed in U.S. patent application Ser. No. 14/822,779, entitled "Implantable Medical Device Coating for Wetting and Microbial Resistance," filed on Aug. 10, 2015; U.S. patent application Ser. No. 14/255,738, entitled "Medical Implant Having a Conductive Coating," filed on Apr. 17, 2014; U.S. patent application Ser. No. 13/680,590, entitled "Fibrous Matrix Coating Materials," filed on Nov. 19, 2012; and/or U.S. Pat. No. 9,364,662, entitled "Implantable Lead Having a Lumen with a Wear-Resistant Liner, the disclosures of which are hereby expressly incorporated herein by reference. In an embodiment after a photosensitive indicator tag 204 has reached the end of its useful life another photosensitive indicator tag 204 may implanted, however other elements of system are reused by the replaced photosensitive indicator tag 204.

The optical sensor 206 is configured to sense at least a portion of the emanated light from the indicator tag 204. In embodiments, the optical sensor 206 may be configured to sense the intensity of the emanated light and/or the color of the emanated light. The optical sensor 206 may be, for example, a photodetector. In embodiments, the optical sensor 206 may include a single sensor configured to sense a single narrowband of wavelengths. Alternatively, in embodiments, the optical sensor 206 may include a plurality of sensors, such that each sensor senses a respective narrowband of wavelengths. In embodiments, the optical sensor 206 may include one or more filters that filter out one or more wavelengths of light, so that only a specific narrowband of wavelength is sensed by the optical sensor 206.

In embodiments, one or more waveguides may couple the emanated light from the indicator tag 204 to the optical sensor 206. In embodiments where the emanated light includes more than one narrowband of wavelengths of light, a single waveguide may couple the emanated light from the indicator tag 204 to the optical sensor 206. Alternatively, a respective waveguide for each narrowband of wavelengths may couple the emanated light from the indicator tag 204 to the optical sensor 206. In embodiments, the one or more waveguides may be configured for dual directionality. That is, a waveguide may couple energy from the light source 202 to the indicator tag 204 and from the indicator tag 204 to the optical sensor 206. In embodiments, the one or more waveguides may include one or more filters for filtering out one or more wavelengths of light.

In embodiments, the light source 202, optical sensor 206 and indicator tag 204 may operate within the visible light spectrum. In other embodiments, the light source 202, optical sensor 206 and indicator tag 204 may operate within the infrared spectrum. In yet other embodiments, the light source 202, optical sensor 206 and indicator tag 204 may operate within the ultraviolet spectrum. In still other embodiments, the light source 202, optical sensor 206 and indicator tag 204 may operate within a combination of the visible, infrared and/or ultraviolet light spectrum. Accordingly, in embodiments, the scope of the term light in this application includes the infrared, visible and ultraviolet portions of the electromagnetic spectrum.

After the optical sensor 206 senses at least a portion of the emanated light from the indicator tag 204, one or more signals corresponding to the sensed emanated light may be sent to and received by the analysis component 208. From the received signals, the analysis component 208 may determine the presence or absence of an analyte and/or an analyte concentration.

As described above, in response to the presence or absence of an analyte and/or an analyte concentration, the indicator tag 204 may change the amount of light that emanates from the indicator tag 204. For example, the amount of light the indicator tag 204 reflects, the fluorescence of the indicator tag 204 and/or the fluorescence lifetime effect of the indicator tag 204 may change in response to the presence or absence of an analyte and/or an analyte concentration.

Figure 4:
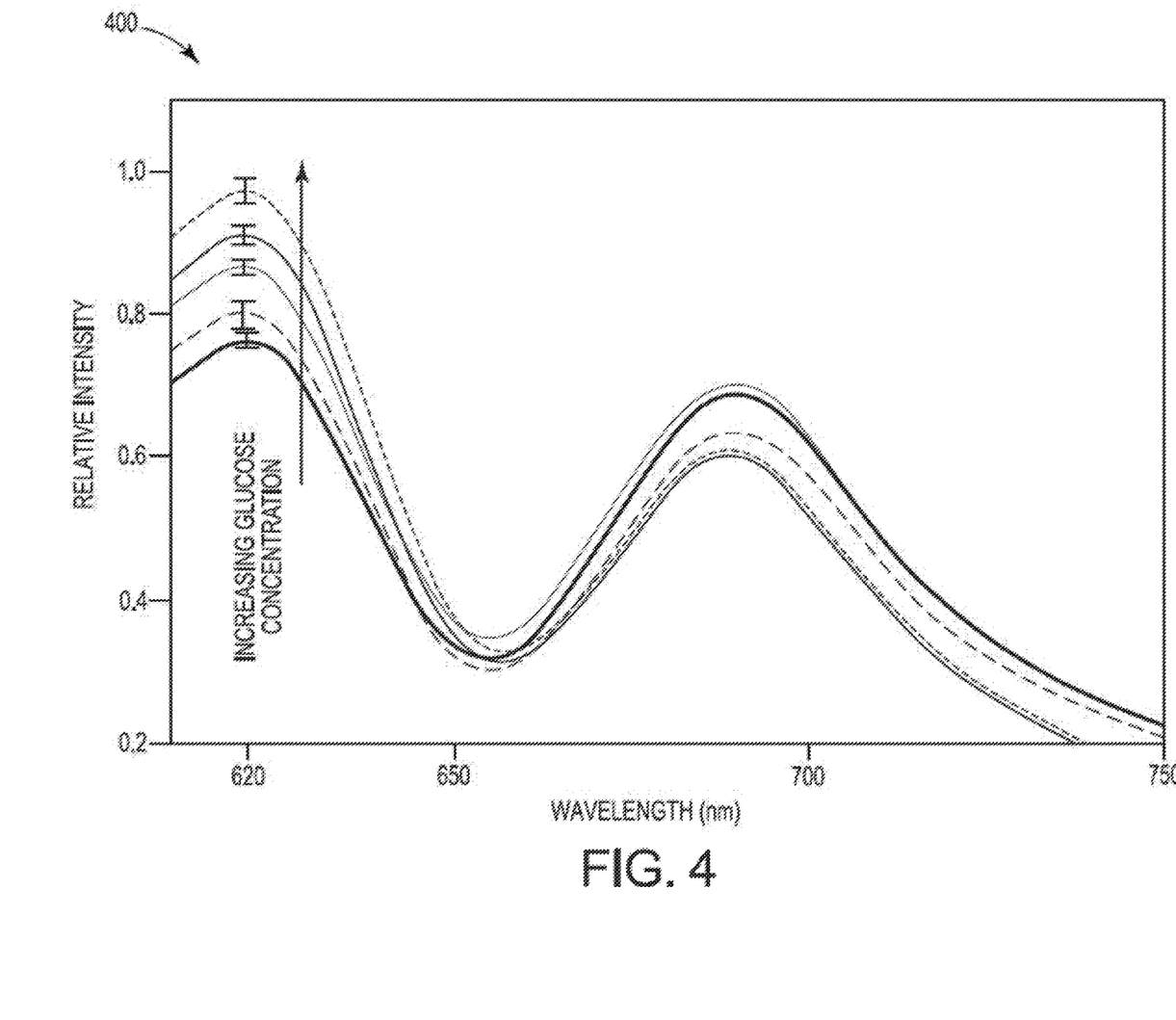
FIG. 4 is a graph depicting relative intensities in response to different analyte concentrations for different wavelengths of light.

For example, in embodiments where the indicator tag 204 changes the amount of light that it reflects in response to an analyte and/or analyte concentration, the analysis component 208 may determine a ratio between the intensity and/or the wavelength of the received light by the optical sensor 206, from the indicator tag 204, and the intensity and/or the wavelength of the emitted light from the light source 202. The analysis component 208 may then correlate the ratio to the presence or absence of an analyte, and/or specific analyte concentration to which the indicator tag 204 responds. A graph depicted relative intensities in response to different analyte concentrations (i.e., glucose) for different wavelengths of light is depicted in FIG. 4 below.

In embodiments, the analysis component 208 may determine the ratio of received light to emitted light for more than one narrowband of wavelengths and compare the ratios for the different narrowbands of wavelengths. By determining ratios of received light to emitted light for multiple narrowbands of wavelengths and comparing the ratios to one another, the analysis component 208 may determine whether the output of the light source 202 has changed and/or whether there are any path loss changes.

For example, assume the absorption of a first wavelength by the indicator tag 204 decreases as an analyte concentration increases and the absorption of a second wavelength stays relatively constant for different concentrations of analytes. Further assume the light emitted from the light source 202 is not measured each time light is emitted, but instead is assumed to be constant. Finally, assume that the intensity of the emitted light has decreased and/or the path loss of the light has increased. As such, if only the ratio of the first wavelength, which is dependent on the analyte concentration, were determined, the ratio would be skewed down and the analyte concentration measurement would be skewed up because less light would be received due to the decreasing intensity of the emitted light and/or due to the increasing path loss for the light. The analysis component 208 may be unable to determine whether the decrease in the ratio was due to an increase in concentration of the analyte, a change in intensity of emitted light and/or a path loss change. On the contrary, if two different ratios were computed for the two different wavelengths, the analysis component 208 may determine whether the intensity of the emitted light has decreased and/or the path loss of the light has increased. That is, the ratio of the received light to the emitted light for the second wavelength would be skewed down. However, the ratio of the received light to the emitted light should be constant because the second wavelength is independent of the analyte concentration. Accordingly, the analysis component 208 could correct the ratio of the received light to the emitted light for the first wavelength based on the skewed ratio for the second wavelength. The analysis component 208 can, therefore, determine the analyte concentration based on the corrected ratio for the first wavelength.

Additionally or alternatively, in embodiments, the analysis component 208 may determine the presence or absence of an analyte and/or an analyte concentration based on the fluorescence of the indicator tag 204. That is, the analysis component 208 may determine a fluorescence that is emitted by the indicator tag 204 and sensed by the optical sensor 206 in response to the indicator tag 204 being stimulated by light emitted from the light source 202. After which, the analysis component may correlate the fluorescence emanated by the indicator tag 204 to the presence or absence of an analyte and/or an analyte concentration to which the indicator tag 204 responds. In embodiments, the light emitted from the light source 202 may include more than one wavelength and the plurality of wavelengths of light may be analyzed by the analysis component 208 to determine whether the changes in emanated light of the indicator tag 204 are due to the presence or absence of an analyte, changes in an analyte concentration, changes in the output intensity of the light source 202 and/or changes in path loss changes, as described above.

Additionally or alternatively, in embodiments, the analysis component 208 may determine the presence or absence of an analyte and/or an analyte concentration based on the fluorescence lifetime effect of the indicator tag 204. That is, the analysis component 208 may determine a delay in the emanated light by the indicator tag 204 after the indicator tag 204 is stimulated by light emitted from the light source 202. After which, the analysis component may correlate the delay to the presence or absence of an analyte and/or an analyte concentration to which the indicator tag 204 responds. Similarly, in embodiments, the light emitted from the light source 202 may include more than one wavelength and the plurality of wavelengths of light may be analyzed by the analysis component 208 to determine whether the changes in emanated light of the indicator tag 204 are due to changes in the presence or absence of an analyte, a change in analyte concentration, changes in the output intensity of the light source 202 and/or changes in path loss changes, as described above.

In embodiments, the analysis component 208 may be implemented in any combination of hardware, software, and/or firmware, and may be implemented, at least in part, by the processor 210. In embodiments, the processor 210 may be, be similar to, include, or be included in, the processor 106 depicted in FIG. 1. The processor 210 may be any arrangement of electronic circuits, electronic components, processors, program components and/or the like configured to store and/or execute programming instructions, to direct the operation of the other functional components of the IMD 200, for example, execute the instructions of the analysis component 208, and may be implemented, for example, in the form of any combination of hardware, software, and/or firmware.

In embodiments, the sensed emanated light may include one or more light pulses. In embodiments, a first pulse that is received by the analysis component 208 may transition the processor 210 from a lower-power state to a higher-power state. In embodiments, the processor 210 may be configured to transition to a higher-power state when executing the instructions of the analysis component 208. When the processor 210 is configured to be in a higher-power state to analyze the received signals, transitioning from a lower-power state to a higher-power state may conserve power of the IMD 200 and, therefore, may increase the longevity of the IMD 200. Additionally or alternatively, the IMD 200 may be configured to transition from a higher-power state to a lower-power state after executing the instructions of the analysis component 208.

The storage device 212 may be used to store information sensed by the IMD 200 according to some implementations. The storage device 212 may include volatile and/or non-volatile memory, and may store instructions that, when executed by the IMD 200 cause methods and processes to be performed by the IMD 200. In embodiments, the processor 210 may process instructions and/or data stored in the storage device 212 to: control sensing and/or analysis operations performed by the IMD 200, control communications performed by the IMD 200, and/or the like.

While the light source 202, the optical sensor 206, the analysis component 208, the processor 210 and the storage device 212 are depicted as being incorporated into the IMD 200, in embodiments, the light source 202, the optical sensor 206, the analysis component 208, the processor 210 and the storage device 212 may be external to the IMD 200. For example, the light source 202, the optical sensor 206, the analysis component 208, the processor 210 and the storage device 212 may be incorporated into a different IMD (not shown). Alternatively, the light source 202, the optical sensor 206, the analysis component 208, the processor 210 and the storage device 212 may be located external to a subject. Additionally or alternatively, in embodiments, the light source 202, the optical sensor 206, the analysis component 208, the processor 210 and the storage device 212 may be distributed between multiple devices. That is, for example, the light source 202, the optical sensor 206, the analysis component 208, the processor 210 and the storage device 212 may refer to a number of different light sources, optical sensors, analysis components and/or processors each disposed on (and/or instantiated by) an IMD or an external device.

The communication component 214 may include, for example, circuits, program components, and one or more transmitters and/or receivers for communicating non-wirelessly or wirelessly with one or more devices that are located external the IMD 200 such as, for example, an external light source, an external optical sensor, an external analysis component, an external processor and/or an external storage device. According to various embodiments, the communication component 214 may include one or more transmitters, receivers, transceivers, transducers, and/or the like, and may be configured to facilitate any number of different types of wireless communication such as, for example, radio-frequency (RF) communication, microwave communication, infrared communication, acoustic communication, inductive communication, conductive communication, and/or the like. The communication component 214 may include any combination of hardware, software, and/or firmware configured to facilitate establishing, maintaining, and using any number of communication links. In embodiments, the communication component 214 may facilitate communications with other implanted or external medical devices such as, for example, to facilitate coordinated operations between the medical devices.

In other embodiments, other forms of non-wireless or wireless telemetry may be utilized for communications. For example, in embodiments, other RF telemetry technologies may be employed. Alternatively, and/or additionally, inductive telemetry, acoustic telemetry and/or the like may be employed for communicating with, e.g., an external light source, an external optical sensor, an external analysis component, an external processor and/or an external storage device. In embodiments, conductive telemetry may be employed, in which case, for example, the communication component 214 may interact with one or more sensing/therapy electrode(s) to transmit and/or receive communications encoded in electrical pulses.

The power source 216 provides electrical power to the other operative components (e.g., the light source 202, the optical sensor 206, the analysis component 208, the processor 210, the storage device 212 and/or the communication component 214) of the IMD 200, and may be any type of power source suitable for providing the desired performance and/or longevity requirements of the IMD 200. In various embodiments, the power source 216 may include one or more batteries, which may be rechargeable (e.g., using an external energy source). The power source 216 may include one or more capacitors, energy conversion mechanisms, and/or the like. Power sources for medical devices such as the IMD 200 are well known, and are therefore not discussed in greater detail herein.

Figure 3A:
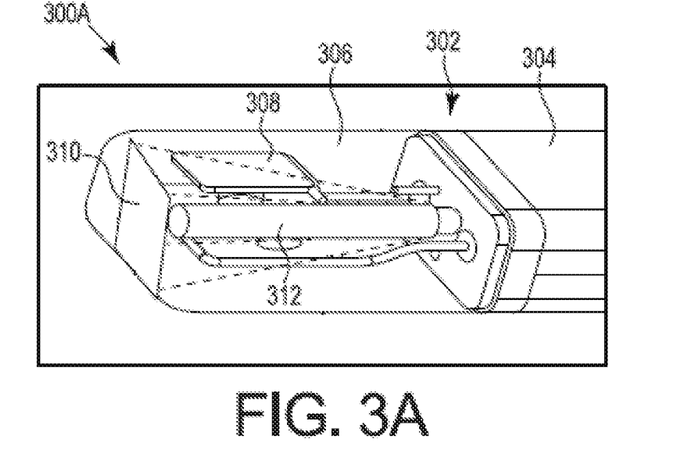
FIGS. 3A-3C are schematic illustrations of portions of IMDs depicting different placements of indicator tags on the IMDs, in accordance with embodiments of the present disclosure.
Figure 3B:
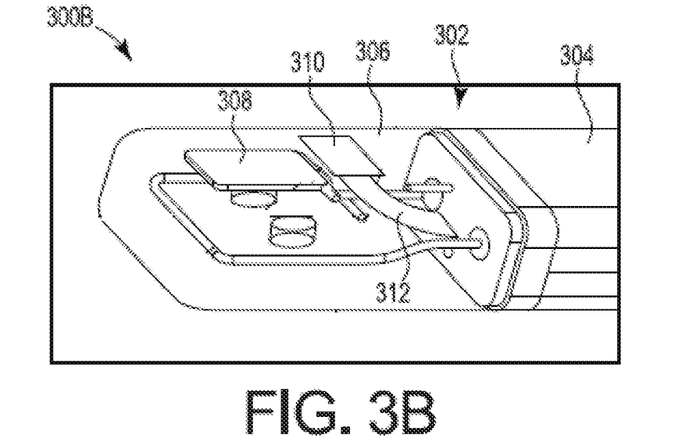
Figure 3C:
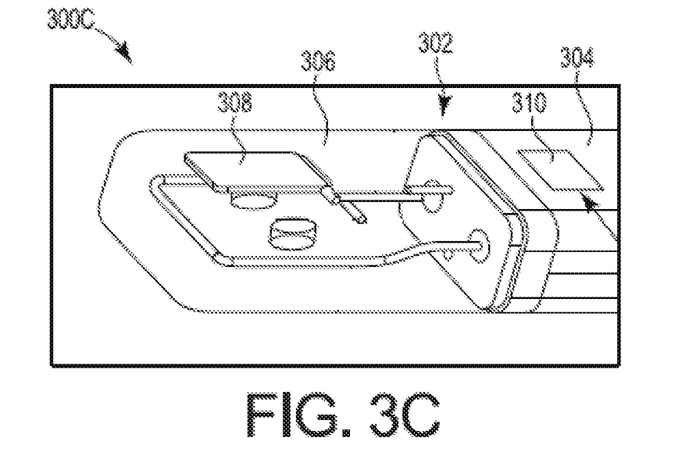

FIGS. 3A-3C are schematic illustrations of portions of IMDs 300A-300C depicting different placements of indicator tags on the IMDs 300A-300C, in accordance with embodiments of the present disclosure. Each of the IMDs 300A-300C may be, be similar to, include, or be included in, the IMD 102 depicted in FIG. 1 and/or the IMD 200 depicted in FIG. 2. For example, the IMD 300A-300C may include a housing 302 having a base portion 304 that includes one or more internal components of the IMD 300A-300C and a header portion 306 that may include any number of electrodes 308 and/or other types of sensors such as, e.g., sound sensors, pressure sensors, impedance sensors, optical sensors, thermometers, barometers, motion or impact sensors (e.g., accelerometers, inertial measuring units (IMUs)), and/or the like) in any number of various types of configurations. In embodiments, the internal components of the IMD 300A-300C may include, for example, a light source (e.g., the light source 118 depicted in FIG. 1 and/or the light source 202 depicted in FIG. 2), an optical sensor (e.g., the optical sensor 120 depicted in FIG. 1 and/or the optical sensor 206 depicted in FIG. 2), an analysis component (e.g., the analysis component 208 depicted in FIG. 3), a processor (e.g., the processor 106 depicted in FIG. 1 and/or the processor 210 depicted in FIG. 2), a storage device (e.g., the storage device 212 depicted in FIG. 2), a communication component (e.g., the communication component 214 depicted in FIG. 2) and/or a power source (e.g., the power source 216 depicted in FIG. 2). In embodiments, however, one or more of these components may be located external to the IMD 300A-300C, for example, in another IMD (not shown), an external device (not shown) and/or the like.

The IMD 300A-300C also includes an indicator tag 310. In embodiments, the indicator tag 310 may have some or all of the same characteristics as the indicator tag 116 and/or the indicator tag 204 depicted in FIGS. 1 and 2, respectively. For example, the indicator 310 is responsive to the presence or absence of an analyte and/or an analyte concentration.

In embodiments, the indicator tag 310 is in communication with the portion of the subject in which the analyte may be present. For example, the indicator tag 310 may be in communication with the subject's interstitial fluid, serous fluid, gastric fluid, blood, urine, an organ, and/or the like that may include the analyte. To do so, the indicator tag 310 may be located on a portion of the IMD 300A-300C such that the indicator tag 310 is in communication the subject's interstitial fluid, serous fluid, gastric fluid, blood, urine, an organ, breath and/or the like that may include the analyte. For example, in embodiments, the indicator tag 310 may be located on a portion of the IMD 300A-300C that is directly exposed to the subject's interstitial fluid, serous fluid, gastric fluid, blood, urine, an organ, and/or the like that may include the analyte. As another example, the indicator tag 310 may be located on a portion of the IMD 300A-300C and covered by a layer that is permeable to the analyte. In embodiments, the indicator tag 310 may be covered by a layer to prolong the useful life of the indicator tag 310.

Referring to FIGS. 3A and 3B, the indicator tag 310 is disposed on different portions of the header 306. In embodiments, the header 306 may be made of a transparent material, for example, a plastic, a glass and/or the like. As such, the header 306 may be used as a waveguide to couple light from one or more internal components of the base portion 304 through the header 306 to the indicator tag 310 and/or from the indicator 310 tag through the header 306 to one or more internal components of the base portion 304. Additionally or alternatively, the header 306 may include a waveguide 312 disposed therein that couples light from the indicator tag 310 to one or more internal components of the base portion 304 and/or from one or more internal components of the base portion 304 to the indicator tag 310. In embodiments, the waveguide 312 may be a glass fiber or a plastic fiber disposed in the header 306. As such, the portion of the header 306 surrounding the fiber 312 may act as a cladding to the fiber. Referring to FIG. 3C, the indicator tag 310 may be disposed on the base portion 304. The base portion 304 may include a window that allows light to be transmitted from one or more internal components of the base portion 304 through the housing 302 to the indicator tag 310 and/or from the indicator tag 310 through the housing 302 to one or more internal components of the base portion 304.

FIG. 4 is a graph 400 depicting relative intensities in response to different analyte concentrations for different wavelengths of light. That is, an indicator tag (e.g., the indicator tag 116 depicted in FIG. 1 and/or the indicator tag 204 depicted in FIG. 2) is disposed in vivo of a subject. The indicator tag was exposed to different narrowbands of wavelengths and different concentrations of an analyte. In this example, the analyte was glucose. This is only one example, however, and the embodiments disclosed herein may be used for any indicator tag that changes one or more of its properties in response a changing analyte concentration. In this example, the analyte is glucose. In response to the different concentrations of glucose, the ratio of the intensity of light emanated by the indicator tag to the intensity of light that the indicator tag was exposed to varied for different narrowbands of wavelengths. For example, at a wavelength of approximately 620 nanometers (nm) (i.e., red light), the ratio of the amount of light emanated by the indicator tag to the amount of light that the indicator tag was exposed to increased, as the concentration of glucose that the indicator tag was exposed to increased. In embodiments, this ratio may be determined by an analysis component (e.g., the analysis component 208 of FIG. 2) based on the known output of the light source and the received light from the optical sensor (e.g., the optical sensor 120 depicted in FIG. 1 and/or the optical sensor 206 depicted in FIG. 2). Furthermore, in embodiments, this ratio may be correlated by, for example, an analysis component to determine the glucose concentration near the indicator tag. As another example, at a wavelength of approximately 650 nm, the ratio of the amount of light emanated by the indicator tag to the amount of light that the indicator tag was exposed to is relatively independent of the concentration of glucose to which the indicator tag is exposed. In embodiments, however, the ratio at 650 nm may be used in conjunction with the ratio at 620 nm to determine whether the increase or decrease in the ratio at 620 nm is due to a varying concentration of glucose, a path loss change and/or a change in intensity of the light output by the light source, as described above.

Figure 5:
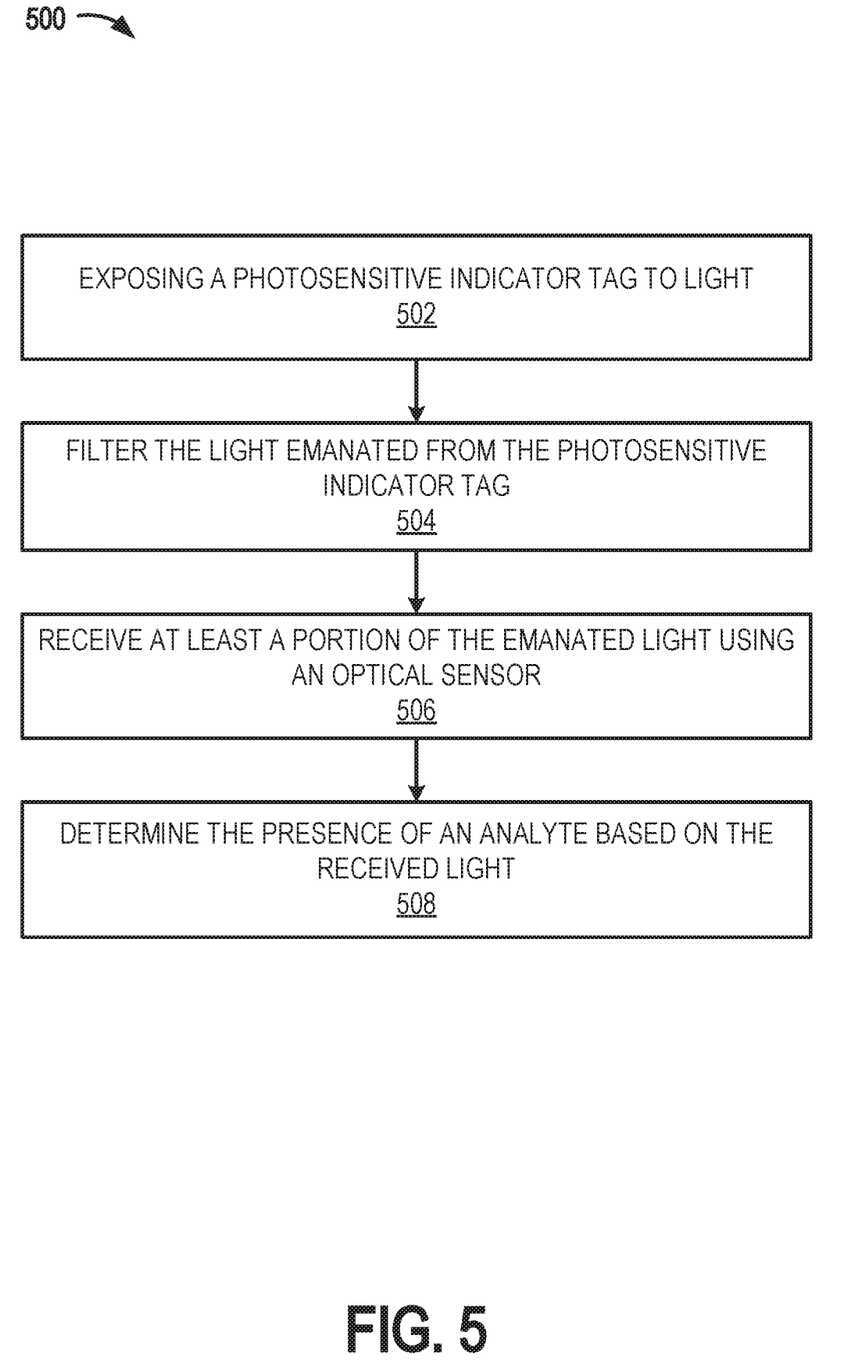
FIG. 5 is a flow diagram depicting an illustrative process for determining the presence of an analyte and/or an analyte concentration, in accordance with embodiments of the present disclosure.

FIG. 5 is a flow diagram depicting an illustrative method 500 for determining the presence or absence of an analyte and/or an analyte concentration, in accordance with embodiments of the present disclosure. The method 500 includes exposing an indicator tag to light (block 502). In embodiments, the light may be emitted from a light source. The light source may be, be similar to, include, or be included in the light source 118 depicted in FIG. 1 and/or the light source 202 depicted in FIG. 2. For example, the light may include one narrowband of wavelengths or more than one narrowbands of wavelengths. As another example, the light source may be included in an IMD, included in a second IMD that is different than the IMD including the indicator tag or included in an external device, i.e., a device not implanted within a subject.

In embodiments, the indicator tag may be, be similar to, include, or be included in the indicator tag 116 depicted in FIG. 1 and/or the indicator tag 204 depicted in FIG. 2. For example, the photosensitive tag may include one or more than one indicator tag. As another example, an IMD may include the indicator tag. As even another example, the indicator tag may emanate light in response to being exposed to light, such that the emanated light corresponds to the presence or absence of an analyte and/or an analyte concentration in which the indicator tag is in contact. Additionally, in embodiments, the emanated light may include one narrowband of wavelengths or more than one narrowbands of wavelengths.

In embodiments, the method 500 may further comprise filtering light that is emanated from the indicator tag (block 504). Filtering the emanated light may be, be similar to, include, or be included in the filters described above in relation to FIG. 2. For example, the indicator tag, a waveguide coupling the light source to the indicator tag, an optical sensor and/or a waveguide coupling the indicator tag to the optical sensor may include one or more filters for filtering out wavelengths of light. In embodiments, the filters may filter out all light except for a narrowband of wavelengths.

In embodiments, the method 500 may further comprise receiving light of the emanated light using an optical sensor (block 506). In embodiments, the optical sensor may be, be similar to, include, or be included in the optical sensor 206 depicted in FIG. 2 above. For example, the optical sensor may be included in the IMD that includes the indicator tag, may be external to the IMD that includes the indicator tag, or may be included in an external device. As another example, the optical sensor may be a photodetector and may include a single sensor configured to sense a single narrowband of wavelengths, or may include a plurality of sensors, such that each sensor of the plurality of sensors senses a respective narrowband of wavelengths. As stated above, in embodiments, the optical sensor may include one or more filters that filter out one or more wavelengths of light. Further, in embodiments, a waveguide may couple the light emanated from the indicator tag to the optical sensor.

In embodiments, the light source, optical sensor and indicator tag of method 500 may operate within the visible light spectrum. In other embodiments, the light source, optical sensor and indicator tag of method 500 may operate within the infrared spectrum. In yet other embodiments, the light source, optical sensor and indicator tag of method 500 may operate within the ultraviolet spectrum. In still other embodiments, the light source, optical sensor and indicator tag of method 500 may operate within a combination of the visible, infrared and/or ultraviolet light spectrum. Accordingly, in embodiments, the scope of the term light in this application includes the infrared, visible and ultraviolet portions of the electromagnetic spectrum.

In embodiments, the method 500 may further comprise determining, using a processor, the presence or absence of an analyte and/or an analyte concentration based on the received light from the optical sensor (block 508). In embodiments, the processor may be, be similar to, include, or be included in the processor 106 depicted in FIG. 1 and/or the processor 210 depicted in FIG. 2. For example, the processor may be included in the IMD that includes the indicator tag, may be external to the IMD that includes the indicator tag, or may be included in an external device. In embodiments, determining the presence or absence of an analyte and/or an analyte concentration of the received light may be, be similar to, include, or be included determining an analyte concentration as discussed above in relation to FIGS. 1, 2 and 4.

For example, determining the presence or absence of an analyte and/or an analyte concentration may include determining a ratio between the intensity of the received light from the optical sensor and the emitted light from the light source. The ratio may then be correlated to the presence or absence of an analyte and/or an analyte concentration to which the indicator tag is exposed. As another example, determining the presence or absence of an analyte and/or an analyte concentration may include may include determining the ratio of received light to emitted light for one or more narrowbands of wavelengths and comparing the ratios for the different narrowbands of wavelengths. The comparison may be correlated to the presence or absence of an analyte and/or an analyte concentration. As even another example, the fluorescence of the indicator tag may change in response to the presence or absence of an analyte and/or an analyte concentration. The fluorescence emanated by the indicator tag may be correlated to the presence or absence of an analyte and/or an analyte concentration. As even another example, the fluorescence lifetime effect of the indicator tag 204 may change in response to the presence or absence of an analyte and/or an analyte concentration. That is, the emanated light by the indicator tag 204 may be delayed by different times that correspond to the presence or absence of an analyte and/or an analyte concentration. The delay may then be correlated to the presence or absence of an analyte and/or an analyte concentration.

Using various embodiments described herein, the presence or absence of an analyte and/or an analyte concentration in vivo of a subject may be determined. Based on the presence or absence of an analyte and/or an analyte concentration, one or more medical conditions may be determined and, in some cases, corrective action may be taken.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A medical system comprising:
    an implantable medical device comprising an indicator tag, wherein the indicator tag is responsive to an analyte;
    a light source configured to emit light onto the indicator tag, wherein the emitted light comprises at least one wavelength of light and wherein the indicator tag emanates light, in response to the emitted light, that corresponds to whether the indicator tag is exposed the analyte;
    an optical sensor configured to receive light, the received light comprising at least a portion of the emanated light, wherein the received light comprises at least one wavelength of light; and
    a processor communicatively coupled to the optical sensor, wherein the processer is configured to determine whether the indicator tag is exposed to the analyte by determining a ratio of an intensity of the portion of the emanated light from the indicator tag to an intensity of the emitted light.

2. The medical system of claim 1, wherein the light source and the optical sensor are incorporated into the implantable medical device.

3. The medical system of claim 1, wherein the light source is incorporated into a different device than the implantable medical device; and wherein the optical sensor is incorporated into the implantable medical device.

4. The medical system of claim 3, wherein the implantable medical device comprises a waveguide configured to transmit the received light to the optical sensor.

5. The medical system of claim 1, wherein the light source is incorporated into the implantable medical device and the optical sensor is incorporated into a different device than the implantable medical device.

6. The medical system of claim 5, wherein the implantable medical device comprises a waveguide configured to transmit the emitted light to the indicator tag.

7. The medical system of claim 1, wherein the light source and the optical sensor are incorporated into a different device than the implantable medical device.

8. The medical system of claim 1, wherein the optical sensor comprises a plurality of photodetectors, wherein each of the plurality of photodetectors are coupled to a respective filter of a plurality of filters, wherein a filter of the plurality of filters is configured to allow only one wavelength of light to pass through the filter.

9. The medical system of claim 1, wherein the processor is configured to determine whether the indicator tag is exposed to the analyte based on the received light by determining a ratio of a wavelength of the received light to a wavelength of the emitted light.

10. The medical system of claim 1,
    wherein the emitted light and the received light comprise at least two wavelengths of light; and
    wherein the processor is configured to determine whether the indicator tag is exposed to the analyte based on the received light by: determining a first absorption of a first wavelength of the at least two wavelengths of light by the indicator tag, determining a second absorption of a second wavelength of the at least two wavelengths of light by the indicator tag and comparing the first absorption to the second absorption.

11. The medical system of claim 1,
    wherein the indicator tag is responsive to the presence of the analyte by changing the indicator tag's fluorescence when exposed the analyte; and wherein the processor is configured to determine whether the indicator tag is exposed to the analyte based on the received light by determining the indicator tag's fluorescence based on the received light.

12. The medical system of claim 1, wherein the processor is configured to determine whether the indicator tag is exposed to the analyte based on the received light by determining a fluorescence lifetime effect of the received light.

13. The medical system of claim 1, wherein the emitted light comprises at least two pulses of light; wherein the received light comprises a first received light pulse, the first received light pulse comprising a light pulse emanated by the indicator tag in response to a first emitted light pulse of the at least two pulses of light; and wherein the processor is configured to transition to a higher-power state in response to the optical sensor receiving the first received light pulse.

14. A method comprising:
exposing an indicator tag to light, wherein the light comprises at least one wavelength of light, wherein the indicator tag emanates light, in response to being exposed to the light, and wherein the emanated light corresponds to whether the indicator tag is exposed the analyte;
receiving at least a portion of the emanated light using an optical sensor, wherein the received light comprises at least one wavelength of light; and
determining, using a processor, whether the indicator tag is exposed to the analyte based on the received light by determining a ratio of an intensity of the portion of the emanated light from the indicator tag to an intensity of the emitted light.

15. The method of claim 14, wherein the exposed light and the received light comprise at least two wavelengths of light and wherein whether the indicator tag is exposed to the analyte based on the received light comprises: determining a first absorption of a first wavelength of the at least two wavelengths by the indicator tag, determining a second absorption of a second wavelength of the at least two wavelengths by the indicator tag and comparing the first absorption to the second absorption.

16. The method of claim 14, wherein the indicator tag is responsive to the presence of the analyte by changing the indicator tag's fluorescence when exposed to different concentrations of the analyte and wherein determining whether the indicator tag is exposed to the analyte based on the received light comprises at least one of: determining the indicator tag's fluorescence based on the received light and determining a fluorescence lifetime effect of the received light.

17. The method of claim 14, wherein determining the presence of the analyte based on the received light comprises determining a fluorescence lifetime effect of the received light.

18. The method of claim 14, wherein at least one of: the optical sensor and the indicator tag are coupled together using a waveguide, and the light source and the indicator tag are coupled together using a waveguide.

19. The method of claim 14, further comprising: filtering the emanated light using at least one filter before the emanated light is received by the optical sensor.

20. The method of claim 14,
wherein the light comprises at least two pulses of light;
wherein the received light comprises a first received light pulse, the first received light pulse comprising a light pulse emanated by the indicator tag in response to a first emitted light pulse of the at least two pulses of light; and
sending a signal to the processor in response to the optical sensor receiving the first received light pulse, wherein the processor transitions from a lower-power state to a higher-power state in response to receiving the signal.

* * * * *